(12) United States Patent
Jimenez et al.

(10) Patent No.: US 12,114,905 B2
(45) Date of Patent: Oct. 15, 2024

(54) REINFORCEMENT AND STRESS RELIEF FOR AN IRRIGATED ELECTROPHYSIOLOGY BALLOON CATHETER WITH FLEXIBLE-CIRCUIT ELECTRODES

(71) Applicant: BIOSENSE WEBSTER (ISRAEL) LTD., Yokneam (IL)

(72) Inventors: Jose Jimenez, Ontario, CA (US); Audrey Vu, Garden Grove, CA (US); Jasson Rodriguez, Los Angeles, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 125 days.

(21) Appl. No.: 17/459,276

(22) Filed: Aug. 27, 2021

(65) Prior Publication Data

US 2023/0061561 A1 Mar. 2, 2023

(51) Int. Cl.
*A61B 18/14* (2006.01)
*A61B 18/00* (2006.01)
*A61M 25/10* (2013.01)

(52) U.S. Cl.
CPC .......... *A61B 18/00* (2013.01); *A61B 18/1492* (2013.01); *A61M 25/1029* (2013.01); *A61B 2018/00029* (2013.01); *A61B 2018/0022* (2013.01); *A61B 2018/00375* (2013.01);
(Continued)

(58) Field of Classification Search
CPC .... A61B 2018/0022; A61B 2018/0016; A61B 2018/00214; A61B 2018/00577; A61B 2018/00285; A61B 2018/00238; A61B 5/6853; A61B 2218/002
See application file for complete search history.

(56) References Cited

U.S. PATENT DOCUMENTS

| | | |
|---|---|---|
| D123,782 S | 12/1940 | Lux |
| 3,316,896 A | 5/1967 | Thomasset |
| 4,232,676 A | 11/1980 | Herczog |

(Continued)

FOREIGN PATENT DOCUMENTS

| | | |
|---|---|---|
| CN | 101422637 A | 5/2009 |
| CN | 102271607 A | 12/2011 |

(Continued)

OTHER PUBLICATIONS

European Search Report for European Application No. 19183327, dated Nov. 21, 2019, 8 pages.

(Continued)

*Primary Examiner* — Jaymi E Della
(74) *Attorney, Agent, or Firm* — Calderon Safran & Wright P.C.; Etan S. Chatlynne

(57) ABSTRACT

A catheter balloon includes a membrane having a proximal end and a distal end. A plurality of substrates are bonded about the membrane. The ability of a bond's ability to withstand repeated stresses during use may be improved by using a reinforcement or a stress relief, while also minimizing the overall thickness of the balloon proximate to its distal end. The reinforcement may comprise a portion of an unassembled membrane. Alternatively, the reinforcement may comprise an adhesive-margin tip. The stress relief may be a serpentine portion of a distal tail of a substrate.

11 Claims, 12 Drawing Sheets

(52) U.S. Cl.
CPC ............... *A61B 2018/00577* (2013.01); *A61B 2562/164* (2013.01); *A61M 2025/105* (2013.01)

(56) References Cited

U.S. PATENT DOCUMENTS

| | | | |
|---|---|---|---|
| 4,276,874 A | 7/1981 | Wolvek et al. | |
| 4,587,975 A | 5/1986 | Salo et al. | |
| 4,709,698 A | 12/1987 | Johnston et al. | |
| 4,805,621 A | 2/1989 | Heinze et al. | |
| 5,178,957 A | 1/1993 | Kolpe et al. | |
| 5,391,199 A | 2/1995 | Ben-Haim | |
| 5,429,617 A | 7/1995 | Hammersmark et al. | |
| 5,582,609 A | 12/1996 | Swanson et al. | |
| 5,584,830 A | 12/1996 | Ladd et al. | |
| 5,702,386 A | 12/1997 | Stern et al. | |
| 5,797,903 A | 8/1998 | Swanson et al. | |
| 5,860,974 A | 1/1999 | Abele | |
| 5,971,983 A | 10/1999 | Lesh | |
| 6,012,457 A | 1/2000 | Lesh | |
| 6,024,740 A | 2/2000 | Lesh et al. | |
| 6,042,580 A | 3/2000 | Simpson | |
| 6,123,718 A | 9/2000 | Tu et al. | |
| 6,142,993 A | 11/2000 | Whayne et al. | |
| 6,164,283 A | 12/2000 | Lesh | |
| 6,171,275 B1 | 1/2001 | Webster, Jr. | |
| 6,176,832 B1 | 1/2001 | Habu et al. | |
| 6,226,542 B1 | 5/2001 | Reisfeld | |
| 6,239,724 B1 | 5/2001 | Doron et al. | |
| 6,301,496 B1 | 10/2001 | Reisfeld | |
| 6,325,777 B1 | 12/2001 | Zadno-Azizi et al. | |
| 6,332,089 B1 | 12/2001 | Acker et al. | |
| 6,380,957 B1 | 4/2002 | Banning | |
| 6,402,740 B1 | 6/2002 | Ellis et al. | |
| D462,389 S | 9/2002 | Provence et al. | |
| 6,471,693 B1 | 10/2002 | Carroll et al. | |
| 6,484,118 B1 | 11/2002 | Govari | |
| 6,522,930 B1 | 2/2003 | Schaer et al. | |
| 6,618,612 B1 | 9/2003 | Acker et al. | |
| 6,656,174 B1 | 12/2003 | Hegde et al. | |
| 6,690,963 B2 | 2/2004 | Ben-Haim et al. | |
| 6,814,733 B2 | 11/2004 | Schwartz et al. | |
| 6,892,091 B1 | 5/2005 | Ben-Haim et al. | |
| 6,893,433 B2 | 5/2005 | Lentz | |
| 6,986,744 B1 | 1/2006 | Krivitski | |
| 6,997,924 B2 | 2/2006 | Schwartz et al. | |
| 7,156,816 B2 | 1/2007 | Schwartz et al. | |
| 7,340,307 B2 | 3/2008 | Maguire et al. | |
| 7,442,190 B2 | 10/2008 | Abboud et al. | |
| 7,536,218 B2 | 5/2009 | Govari et al. | |
| 7,756,576 B2 | 7/2010 | Levin | |
| 7,842,031 B2 | 11/2010 | Abboud et al. | |
| 8,048,032 B2 | 11/2011 | Root et al. | |
| 8,231,617 B2 | 7/2012 | Satake | |
| 8,267,932 B2 | 9/2012 | Baxter et al. | |
| 8,357,152 B2 | 1/2013 | Govari et al. | |
| D682,289 S | 5/2013 | Dijulio et al. | |
| D682,291 S | 5/2013 | Baek et al. | |
| D690,318 S | 9/2013 | Kluttz et al. | |
| D694,652 S | 12/2013 | Tompkin | |
| 8,641,709 B2 | 2/2014 | Sauvageau et al. | |
| 8,721,590 B2 | 5/2014 | Seward et al. | |
| 8,777,161 B2 | 7/2014 | Pollock et al. | |
| D716,340 S | 10/2014 | Bresin et al. | |
| 8,852,181 B2 | 10/2014 | Malecki et al. | |
| D720,766 S | 1/2015 | Mandal et al. | |
| D721,379 S | 1/2015 | Moon et al. | |
| D724,618 S | 3/2015 | Shin | |
| 8,974,450 B2 | 3/2015 | Brannan | |
| 8,998,893 B2 | 4/2015 | Avitall | |
| D729,263 S | 5/2015 | Ahn et al. | |
| 9,089,350 B2 | 7/2015 | Willard | |
| D736,780 S | 8/2015 | Wang | |
| 9,126,023 B1 | 9/2015 | Sahatjian et al. | |
| D740,308 S | 10/2015 | Kim et al. | |
| D743,424 S | 11/2015 | Danielyan et al. | |
| D744,000 S | 11/2015 | Villamor et al. | |
| 9,173,758 B2 | 11/2015 | Brister et al. | |
| D747,742 S | 1/2016 | Fan et al. | |
| D750,644 S | 3/2016 | Bhutani et al. | |
| 9,283,034 B2 | 3/2016 | Katoh et al. | |
| 9,289,141 B2 | 3/2016 | Lowery et al. | |
| D753,690 S | 4/2016 | Vazquez et al. | |
| 9,320,631 B2 | 4/2016 | Moore et al. | |
| 9,345,540 B2 | 5/2016 | Mallin et al. | |
| D759,673 S | 6/2016 | Looney et al. | |
| D759,675 S | 6/2016 | Looney et al. | |
| D764,500 S | 8/2016 | Wang | |
| D765,709 S | 9/2016 | Gagnier | |
| D767,616 S | 9/2016 | Jones et al. | |
| D768,696 S | 10/2016 | Gagnier | |
| D783,037 S | 4/2017 | Hariharan et al. | |
| 9,655,677 B2 | 5/2017 | Salahieh et al. | |
| D791,805 S | 7/2017 | Segars | |
| 9,795,442 B2 | 10/2017 | Salahieh et al. | |
| D861,717 S | 10/2019 | Brekke et al. | |
| 10,688,278 B2 | 6/2020 | Beeckler et al. | |
| 2001/0031961 A1 | 10/2001 | Hooven | |
| 2002/0002369 A1 | 1/2002 | Hood | |
| 2002/0065455 A1 | 5/2002 | Ben-Haim et al. | |
| 2002/0077627 A1 | 6/2002 | Johnson et al. | |
| 2002/0160134 A1 | 10/2002 | Ogushi et al. | |
| 2003/0018327 A1 | 1/2003 | Truckai et al. | |
| 2003/0050637 A1 | 3/2003 | Maguire et al. | |
| 2003/0060820 A1 | 3/2003 | Maguire et al. | |
| 2003/0120150 A1 | 6/2003 | Govari | |
| 2004/0068178 A1 | 4/2004 | Govari | |
| 2004/0122445 A1* | 6/2004 | Butler ............... A61B 17/22031 606/127 |
| 2004/0225285 A1 | 11/2004 | Gibson | |
| 2005/0059862 A1 | 3/2005 | Phan | |
| 2005/0070887 A1 | 3/2005 | Taimisto et al. | |
| 2005/0119686 A1 | 6/2005 | Clubb | |
| 2006/0013595 A1 | 1/2006 | Trezza et al. | |
| 2006/0135953 A1 | 6/2006 | Kania et al. | |
| 2007/0071792 A1 | 3/2007 | Varner et al. | |
| 2007/0080322 A1 | 4/2007 | Walba | |
| 2007/0083194 A1 | 4/2007 | Kunis et al. | |
| 2007/0276212 A1 | 11/2007 | Fuimaono et al. | |
| 2007/0287994 A1 | 12/2007 | Patel | |
| 2008/0018891 A1 | 1/2008 | Hell et al. | |
| 2008/0021313 A1 | 1/2008 | Eidenschink et al. | |
| 2008/0051707 A1 | 2/2008 | Phan et al. | |
| 2008/0140072 A1 | 6/2008 | Stangenes et al. | |
| 2008/0183132 A1 | 7/2008 | Davies et al. | |
| 2008/0188912 A1 | 8/2008 | Stone et al. | |
| 2008/0202637 A1 | 8/2008 | Hector et al. | |
| 2008/0249463 A1 | 10/2008 | Pappone et al. | |
| 2008/0262489 A1 | 10/2008 | Steinke | |
| 2009/0163890 A1 | 6/2009 | Clifford et al. | |
| 2009/0171274 A1 | 7/2009 | Harlev et al. | |
| 2009/0182318 A1 | 7/2009 | Abboud et al. | |
| 2009/0270850 A1 | 10/2009 | Zhou et al. | |
| 2010/0069836 A1 | 3/2010 | Satake | |
| 2010/0114269 A1 | 5/2010 | Wittenberger et al. | |
| 2010/0160906 A1 | 6/2010 | Jarrard | |
| 2010/0204560 A1 | 8/2010 | Salahieh et al. | |
| 2010/0256629 A1 | 10/2010 | Wylie et al. | |
| 2010/0324552 A1 | 12/2010 | Kauphusman et al. | |
| 2011/0118632 A1 | 5/2011 | Sinelnikov et al. | |
| 2011/0130648 A1 | 6/2011 | Beeckler et al. | |
| 2011/0282338 A1 | 11/2011 | Fojtik | |
| 2011/0295248 A1 | 12/2011 | Wallace et al. | |
| 2011/0301587 A1 | 12/2011 | Deem et al. | |
| 2011/0313286 A1 | 12/2011 | Whayne et al. | |
| 2012/0019107 A1 | 1/2012 | Gabl et al. | |
| 2012/0029511 A1 | 2/2012 | Smith et al. | |
| 2012/0065503 A1 | 3/2012 | Rogers et al. | |
| 2012/0071870 A1* | 3/2012 | Salahieh ............ A61B 1/00181 606/33 |
| 2012/0079427 A1 | 3/2012 | Carmichael et al. | |
| 2012/0101413 A1 | 4/2012 | Beetel et al. | |
| 2012/0143177 A1 | 6/2012 | Avitall | |
| 2012/0191079 A1 | 7/2012 | Moll et al. | |

(56) References Cited

U.S. PATENT DOCUMENTS

| | | |
|---|---|---|
| 2013/0085360 A1 | 4/2013 | Grunewald |
| 2013/0090649 A1 | 4/2013 | Smith et al. |
| 2013/0109982 A1 | 5/2013 | Sato et al. |
| 2013/0150693 A1 | 6/2013 | D'Angelo et al. |
| 2013/0165916 A1 | 6/2013 | Mathur et al. |
| 2013/0165925 A1* | 6/2013 | Mathur ............... A61B 18/16 606/41 |
| 2013/0165941 A1 | 6/2013 | Murphy |
| 2013/0165990 A1 | 6/2013 | Mathur et al. |
| 2013/0261692 A1 | 10/2013 | Cardinal et al. |
| 2013/0274562 A1 | 10/2013 | Ghaffari et al. |
| 2013/0274658 A1 | 10/2013 | Steinke et al. |
| 2013/0282084 A1 | 10/2013 | Mathur et al. |
| 2013/0318439 A1 | 11/2013 | Landis et al. |
| 2014/0018788 A1 | 1/2014 | Engelman et al. |
| 2014/0031813 A1 | 1/2014 | Tellio et al. |
| 2014/0058197 A1 | 2/2014 | Salahieh et al. |
| 2014/0121470 A1 | 5/2014 | Scharf et al. |
| 2014/0148805 A1 | 5/2014 | Stewart et al. |
| 2014/0227437 A1 | 8/2014 | Deboer et al. |
| 2014/0243821 A1 | 8/2014 | Salahieh et al. |
| 2014/0276756 A1 | 9/2014 | Hill |
| 2014/0276811 A1 | 9/2014 | Koblish et al. |
| 2014/0288546 A1 | 9/2014 | Sherman et al. |
| 2014/0330266 A1 | 11/2014 | Thompson et al. |
| 2014/0357956 A1* | 12/2014 | Salahieh ............ A61N 1/37247 348/77 |
| 2014/0378803 A1 | 12/2014 | Geistert et al. |
| 2015/0005799 A1* | 1/2015 | Lindquist ............ A61B 18/1492 156/272.8 |
| 2015/0018818 A1 | 1/2015 | Willard et al. |
| 2015/0025532 A1 | 1/2015 | Hanson et al. |
| 2015/0025533 A1 | 1/2015 | Groff et al. |
| 2015/0057655 A1 | 2/2015 | Osypka |
| 2015/0067512 A1 | 3/2015 | Roswell |
| 2015/0080883 A1 | 3/2015 | Haverkost et al. |
| 2015/0105774 A1 | 4/2015 | Lindquist et al. |
| 2015/0112256 A1 | 4/2015 | Byrne et al. |
| 2015/0119875 A1 | 4/2015 | Fischell et al. |
| 2015/0141982 A1 | 5/2015 | Lee |
| 2015/0157382 A1 | 6/2015 | Avitall et al. |
| 2015/0216591 A1 | 8/2015 | Cao et al. |
| 2015/0216650 A1 | 8/2015 | Shaltis |
| 2015/0265329 A1 | 9/2015 | Lalonde et al. |
| 2015/0265339 A1 | 9/2015 | Lindquist et al. |
| 2015/0265812 A1 | 9/2015 | Lalonde |
| 2015/0272667 A1 | 10/2015 | Govari et al. |
| 2015/0341752 A1 | 11/2015 | Flynn |
| 2016/0000499 A1 | 1/2016 | Lennox et al. |
| 2016/0051321 A1 | 2/2016 | Salahieh et al. |
| 2016/0085431 A1 | 3/2016 | Kim et al. |
| 2016/0106499 A1 | 4/2016 | Ogata et al. |
| 2016/0166306 A1 | 6/2016 | Pageard |
| 2016/0175041 A1 | 6/2016 | Govari et al. |
| 2016/0183877 A1 | 6/2016 | Williams et al. |
| 2016/0196635 A1 | 7/2016 | Cho et al. |
| 2016/0256305 A1 | 9/2016 | Longo et al. |
| 2016/0374748 A9 | 12/2016 | Salahieh et al. |
| 2017/0042614 A1 | 2/2017 | Salahieh et al. |
| 2017/0042615 A1 | 2/2017 | Salahieh et al. |
| 2017/0080192 A1 | 3/2017 | Giasolli et al. |
| 2017/0143359 A1 | 5/2017 | Nguyen et al. |
| 2017/0164464 A1 | 6/2017 | Weinkam et al. |
| 2017/0311829 A1* | 11/2017 | Beeckler ............ A61B 18/1492 |
| 2017/0311893 A1 | 11/2017 | Beeckler et al. |
| 2017/0312022 A1 | 11/2017 | Beeckler et al. |
| 2017/0347896 A1 | 12/2017 | Keyes et al. |
| 2017/0348049 A1* | 12/2017 | Vrba ............... A61B 18/1492 |
| 2018/0074693 A1 | 3/2018 | Jones et al. |
| 2018/0092688 A1 | 4/2018 | Tegg |
| 2018/0110562 A1 | 4/2018 | Govari et al. |
| 2018/0161093 A1 | 6/2018 | Basu et al. |
| 2018/0256247 A1 | 9/2018 | Govari et al. |
| 2018/0333162 A1 | 11/2018 | Saab |
| 2018/0368927 A1 | 12/2018 | Lyons et al. |
| 2019/0297441 A1 | 9/2019 | Dehe et al. |
| 2019/0298441 A1 | 10/2019 | Clark et al. |
| 2020/0001054 A1* | 1/2020 | Jimenez ............ A61B 18/1492 |
| 2020/0008869 A1 | 1/2020 | Byrd |
| 2020/0015693 A1 | 1/2020 | Beeckler et al. |
| 2020/0085497 A1* | 3/2020 | Zhang ............... A61B 18/1492 |
| 2020/0155226 A1 | 5/2020 | Valls et al. |
| 2021/0169567 A1 | 6/2021 | Govari et al. |

FOREIGN PATENT DOCUMENTS

| | | |
|---|---|---|
| CN | 102458566 A | 5/2012 |
| CN | 203539434 U | 4/2014 |
| CN | 104244856 A | 12/2014 |
| CN | 104546117 A | 4/2015 |
| CN | 105105844 A | 12/2015 |
| CN | 105473091 A | 4/2016 |
| CN | 105473093 A | 4/2016 |
| EP | 0779059 A1 | 6/1997 |
| EP | 1790304 A2 | 5/2007 |
| EP | 2865350 A2 | 4/2015 |
| EP | 2875790 A2 | 5/2015 |
| EP | 3238646 A2 | 11/2017 |
| EP | 3238648 A1 | 11/2017 |
| EP | 3251622 A1 | 12/2017 |
| EP | 3300680 A1 | 4/2018 |
| EP | 3315087 A1 | 5/2018 |
| EP | 3332727 A2 | 6/2018 |
| EP | 3571983 A2 | 11/2019 |
| EP | 3586778 A1 | 1/2020 |
| EP | 3653153 A1 | 5/2020 |
| JP | H06261951 A | 9/1994 |
| JP | H1176233 A | 3/1999 |
| JP | 2000504242 A | 4/2000 |
| JP | 2004504314 A | 2/2004 |
| JP | 2005052424 A | 3/2005 |
| JP | 2008538986 A | 11/2008 |
| JP | 2009261609 A | 11/2009 |
| JP | 2010507404 A | 3/2010 |
| JP | 2010088697 A | 4/2010 |
| JP | 2012024156 A | 2/2012 |
| JP | 2012508083 A | 4/2012 |
| JP | 2013013726 A | 1/2013 |
| JP | 2013078587 A | 5/2013 |
| JP | 2013529109 A | 7/2013 |
| JP | 2014509218 A | 4/2014 |
| JP | 2014529419 A | 11/2014 |
| JP | 2015503365 A | 2/2015 |
| JP | 2015100706 A | 6/2015 |
| JP | 2015112113 A | 6/2015 |
| JP | 2015112114 A | 6/2015 |
| JP | 2015518776 A | 7/2015 |
| JP | 2016093502 A | 5/2016 |
| JP | 2016515442 A | 5/2016 |
| JP | 2016116863 A | 6/2016 |
| JP | 2016534842 A | 11/2016 |
| JP | 2017202305 A | 11/2017 |
| JP | 2017202306 A | 11/2017 |
| JP | 2018075365 A | 5/2018 |
| WO | 9605768 A1 | 2/1996 |
| WO | 0056237 A2 | 9/2000 |
| WO | 02102231 A2 | 12/2002 |
| WO | 2005041748 A2 | 5/2005 |
| WO | 2006055654 A1 | 5/2006 |
| WO | 2008049087 A2 | 4/2008 |
| WO | 2011143468 A2 | 11/2011 |
| WO | 2013049601 A2 | 4/2013 |
| WO | 2013052919 A2 | 4/2013 |
| WO | 2013154776 A2 | 10/2013 |
| WO | 2014123983 A2 | 8/2014 |
| WO | 2014168987 A1 | 10/2014 |
| WO | 2015049784 A1 | 4/2015 |
| WO | 2015200518 A1 | 12/2015 |
| WO | 2016084215 A1 | 6/2016 |
| WO | 2016183337 A2 | 11/2016 |
| WO | 2016210437 A1 | 12/2016 |
| WO | 2017024306 A1 | 2/2017 |
| WO | 2017087549 A1 | 5/2017 |

(56) References Cited

FOREIGN PATENT DOCUMENTS

| WO | 2017163400 A1 | 9/2017 |
|---|---|---|
| WO | 2018106569 A1 | 6/2018 |
| WO | 2019095020 A1 | 5/2019 |

OTHER PUBLICATIONS

Extended European Search Report for Application No. EP17168393.1, dated Dec. 15, 2017, 12 pages.
Extended European Search Report for Application No. EP17168513.4, dated Sep. 18, 2017, 11 pages.
Extended European Search Report for European Application No. 17201434.2, dated Feb. 1, 2018, 9 pages.
Extended European Search Report for European Application No. EP15201723.2, dated May 11, 2016, 7 pages.
Extended European Search Report for European Application No. EP17168518.3, dated Sep. 20, 2017, 9 pages.
Extended European Search Report for European Application No. EP17173893.3, dated Nov. 6, 2017, 8 pages.
Extended European Search Report for European Application No. EP17205876.0, dated Jun. 1, 2018, 13 pages.
Extended European Search Report for European Application No. EP20153872.5, dated May 7, 2020, 8 pages.
Extended European Search Report for European Application No. EP20195648.9, dated Feb. 12, 2021, 8 pages.
International Search Report and Written Opinion for Application No. PCT/IB2019/056381, dated Dec. 17, 2019, 10 pages.
International Search Report and Written Opinion for Application No. PCT/IB2019/052313, dated Jul. 22, 2019, 08 pages.
Partial European Search Report for Application No. EP17168393.1, dated Sep. 13, 2017, 13 pages.
Partial European Search Report for European Application No. EP17205876.0, dated Feb. 22, 2018, 10 pages.
YouTube, "Intensity™ CX4 Professional E-Stim/Ultrasound Combo" Dec. 22, 2015, Retrieved from internet [https://www.youtube.com/watch?v=76s1QKMWJME], retrieved from the internet on Nov. 19, 2020, 1 page.
YouTube, "New Interface TactiCath Contact Force Ablation Catheter", Nov. 26, 2013, retrieved from internet [https://www.youtube.com/watch?v=aYvYO8Hpylg], retrieved on Nov. 19, 2020, 1 page.
Extended European Search Report for European Application No. EP19177365.4, dated Nov. 8, 2019, 7 pages.
Haines, D.E., et al., "The Promise of Pulsed Field Ablation," Dec. 2019, vol. 19 (12), pp. 10.

* cited by examiner

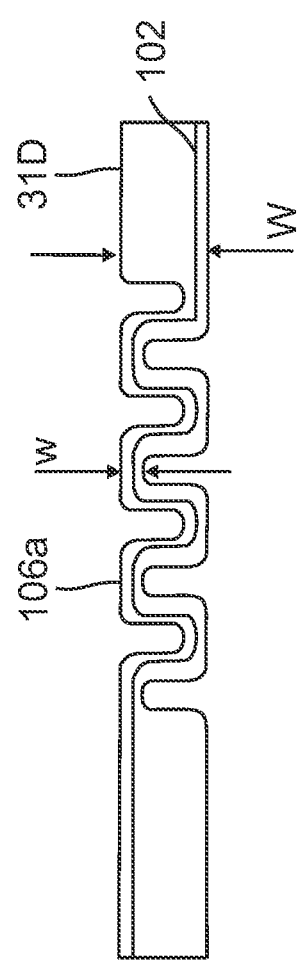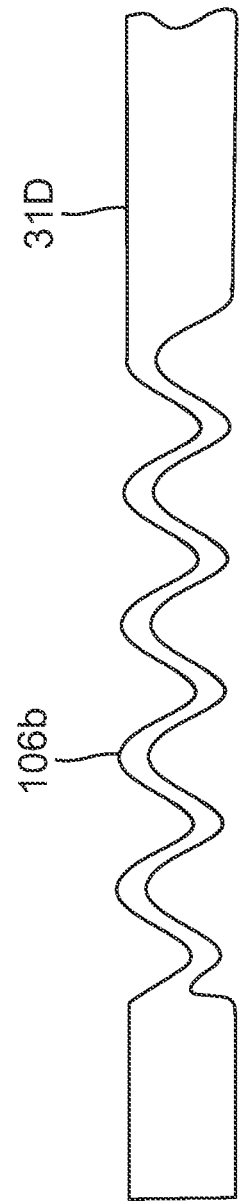
FIG. 11A
FIG. 11B

REINFORCEMENT AND STRESS RELIEF FOR AN IRRIGATED ELECTROPHYSIOLOGY BALLOON CATHETER WITH FLEXIBLE-CIRCUIT ELECTRODES

FIELD

The subject matter disclosed herein relates to electrophysiologic catheters, particularly those capable of ablating cardiac tissue via electrodes disposed on a balloon surface.

BACKGROUND

Ablation of cardiac tissue has been used to treat cardiac arrhythmias. Ablative energies are typically provided to cardiac tissue by a tip portion, which can deliver ablative energy alongside the tissue to be ablated. Some of these catheters administer ablative energy from various electrodes disposed on or incorporated into three-dimensional structures, e.g., wire baskets and balloons.

SUMMARY OF THE DISCLOSURE

Solutions for improving the robustness of a catheter balloon, embodied in assembly techniques, are disclosed. The catheter balloon includes a membrane having a proximal end and a distal end. A plurality of substrates, e.g., ten substrates, are disposed about the membrane. In a first solution, each of the plurality of substrates includes a respective tail terminating at a respective distal tip disposed proximal to the distal end of the membrane. Each of the plurality of substrates may include a plurality of irrigation pores including a distal irrigation pore, such that a distance between each respective distal tip and each respective distal irrigation pore is between about 1 millimeter and about 3 millimeters. An adhesive may be disposed between each of the plurality of substrates and the membrane to bond each substrate to the membrane. The plurality of substrates each include side edges and an adhesive margin is disposed atop the side edges and the membrane. Further, a reinforcement is disposed atop each of the respective distal tips and the membrane. The reinforcement may comprise a portion of an unassembled membrane. Alternatively, the reinforcement may comprise an adhesive-margin tip. For example, a portion of the adhesive-margin tip that contacts the membrane extends from the respective distal tip by between about 0.3 millimeters and about 0.6 millimeters.

This balloon may be incorporated into a catheter comprising a probe and a shaft. Specifically, the balloon may be attached to a distal end of the shaft that may be passed through the probe. The probe may have a lumen having an inner diameter of about 13.5 french. The shaft may include a first shaft portion and a second shaft portion partially disposed within the first shaft portion in a telescoping relationship with the first shaft portion. As such the catheter balloon may be disposed in the lumen such that a proximal end of its membrane is connected to the first shaft portion and a distal end of its membrane is connected to the second shaft portion.

A thickness of the balloon as measured from an inner surface of the membrane, through one of the respective distal tips, and to an outer surface of the reinforcement may be about 0.0075 inches. Such permits the maximum force required to move the shaft in the lumen being less than about 6 lbf.

In a second solution, the substrates may be provided with a stress-relief portion. Specifically, each of the plurality of substrates may include a distal tail. The distal tail may include a portion having a serpentine form. The serpentine form may comprise a square wave or a curved wave. Further the serpentine form may comprise between about three periods and ten periods. Additionally, the width of the serpentine form may be between about 1/10 to about 1/2 of a width of the distal tail.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

FIG. 11A depicts a first exemplary pattern of the stress relief;

FIG. 11B depicts a second exemplary pattern of the stress relief;

MODES OF CARRYING OUT THE INVENTION

The following detailed description should be read with reference to the drawings, in which like elements in different drawings are similarly numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Overview

Ablation of cardiac tissue to correct a malfunctioning heart is a well-known procedure. Typically, to successfully ablate, cardiac electropotentials need to be measured at various locations of the myocardium. In addition, temperature measurements during ablation provide data enabling the efficacy of the ablation to be measured. Typically, for an ablation procedure, the electropotentials and the temperatures are measured before, during, and after the actual ablation.

An ablation catheter may include a lumen, and a balloon may be deployed through the catheter lumen. A multi-layer flexible metal structure is attached to an exterior wall or membrane of the balloon. The structure comprises a plurality of electrode groups arranged circumferentially about the longitudinal axis, where each electrode group comprises multiple ablation electrodes, typically arranged longitudinally.

Each electrode group may also include at least one micro-electrode that is insulated physically and electrically from the ablation electrodes in its group. Each electrode group may also include at least a thermocouple. In some embodiments, each electrode group includes a micro-electrode and a thermocouple formed at a common location. Using a single catheter, with the three functionalities of ability to perform ablation, electropotential measurement, and temperature measurement, simplifies cardiac ablation procedures.

System Description

Figure 1:
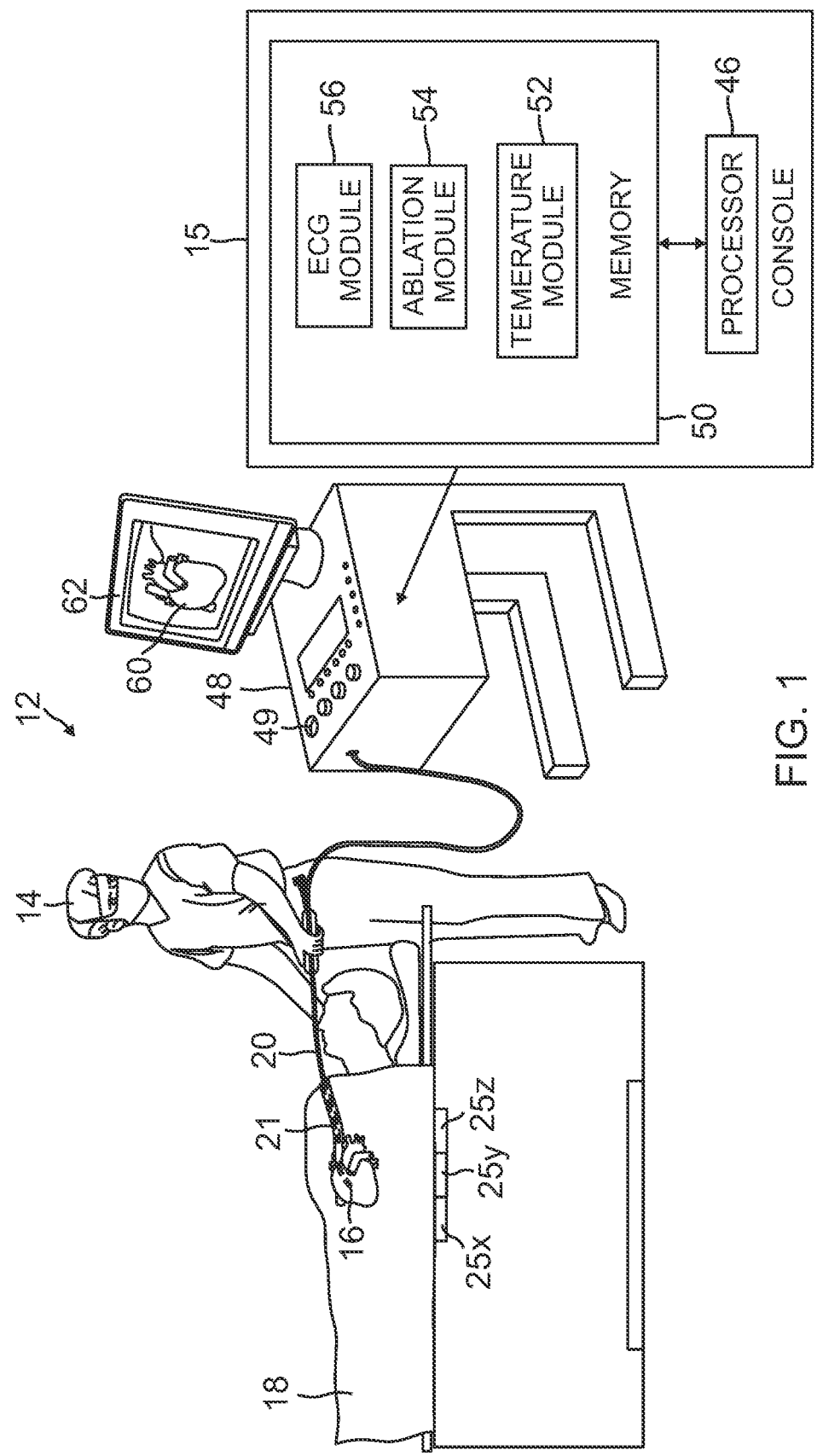
FIG. 1 depicts a schematic illustration of an invasive medical procedure.

FIG. 1 is a schematic illustration of an invasive medical procedure using apparatus 12, according to an embodiment. The procedure is performed by a medical professional 14, and, by way of example, the procedure in the description hereinbelow is assumed to comprise ablation of a portion of a myocardium 16 of the heart of a human patient 18. However, it is understood that embodiments disclosed herein are not merely applicable to this specific procedure, and may include substantially any procedure on biological tissue or on non-biological materials.

Figure 2:
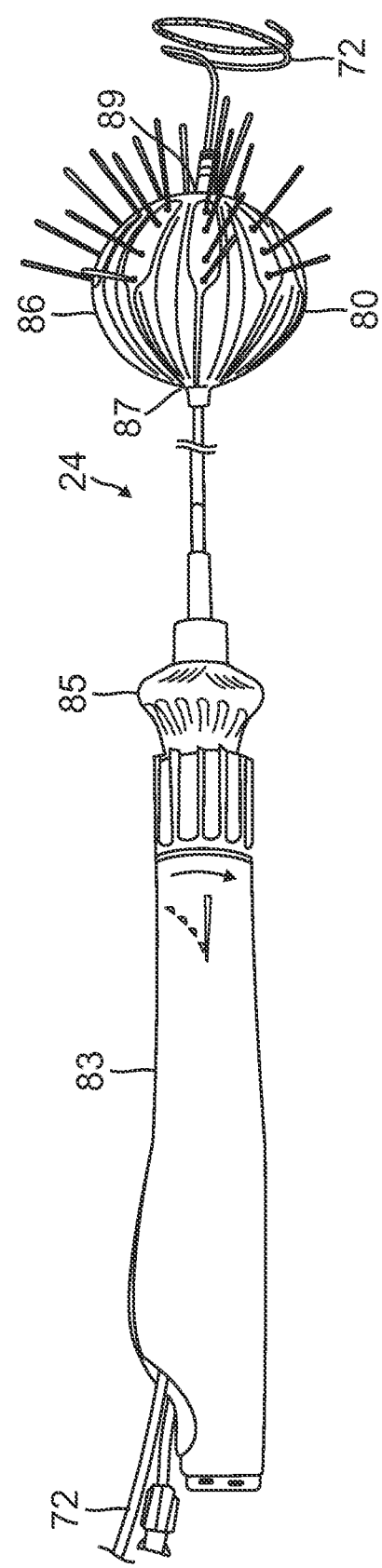
FIG. 2 depicts a top view of a catheter with a balloon in an expanded state, in use with a lasso catheter.

To perform the ablation, medical professional 14 inserts a probe 20 into a sheath 21 that has been pre-positioned in a lumen of the patient. Sheath 21 is positioned so that a distal end 22 of probe 20 enters the heart of the patient. A diagnostic/therapeutic catheter 24 (e.g., a balloon catheter), reflected in FIG. 2, is deployed through a lumen 23 of the probe 20, and exits from a distal end of the probe 20.

As shown in FIG. 1, apparatus 12 is controlled by a system processor 46, which is in an operating console 15 of the apparatus. Console 15 comprises controls 49 which are used by professional 14 to communicate with the processor. During the procedure, the processor 46 typically tracks a location and an orientation of the distal end 22 of the probe 20, using any method known in the art. For example, processor 46 may use a magnetic tracking method, wherein magnetic transmitters 25X, 25Y and 25Z external to the patient 18 generate signals in coils positioned in the distal end of the probe 20. The CARTO® system (available from Biosense Webster, Inc. of Irvine, California) uses such a tracking method.

The software for the processor 46 may be downloaded to the processor in electronic form, over a network, for example. Alternatively, or additionally, the software may be provided on non-transitory tangible media, such as optical, magnetic, or electronic storage media. The tracking of the distal end 22 is may be displayed on a three-dimensional representation 60 of the heart of the patient 18 on a screen 62. However, it may be displayed two-dimensionally, e.g., by fluoroscopy or MRI.

To operate apparatus 12, the processor 46 communicates with a memory 50, which has many modules used by the processor to operate the apparatus. Thus, the memory 50 comprises a temperature module 52, an ablation module 54, and an electrocardiograph (ECG) module 56, the functions of which are described below. The memory 50 typically comprises other modules, such as a force module for measuring the force on the distal end 22, a tracking module for operating the tracking method used by the processor 46, and an irrigation module allowing the processor to control irrigation provided for the distal end 22. For simplicity, such other modules are not illustrated in FIG. 1. The modules may comprise hardware as well as software elements. For example, module 54 may include a radio-frequency generator with at least one output or output channel, e.g., ten outputs or ten output channels. Each of the outputs may be separately and selectively activated or deactivated by a switch. That is, each switch may be disposed between the signal generator and a respective output. Thus, a generator with ten outputs would include ten switches. These outputs may each be individually coupled to electrodes on an ablation catheter, e.g., the ten electrodes 33 on balloon 80, described in further detail below. Such an electrical connection may be achieved by establishing an electrical path between each output and each electrode. For example, each output may be connected to a corresponding electrode by one or more wires or suitable electrical connectors. Thus, in some embodiments, an electrical path may include at least one wire. In some embodiments, the electrical path may further include an electrical connector and at least a second wire. Thus, electrodes 33 may be selectively activated and deactivated with the switches to receive radiofrequency energy separately from each of the other electrodes.

Figure 3:
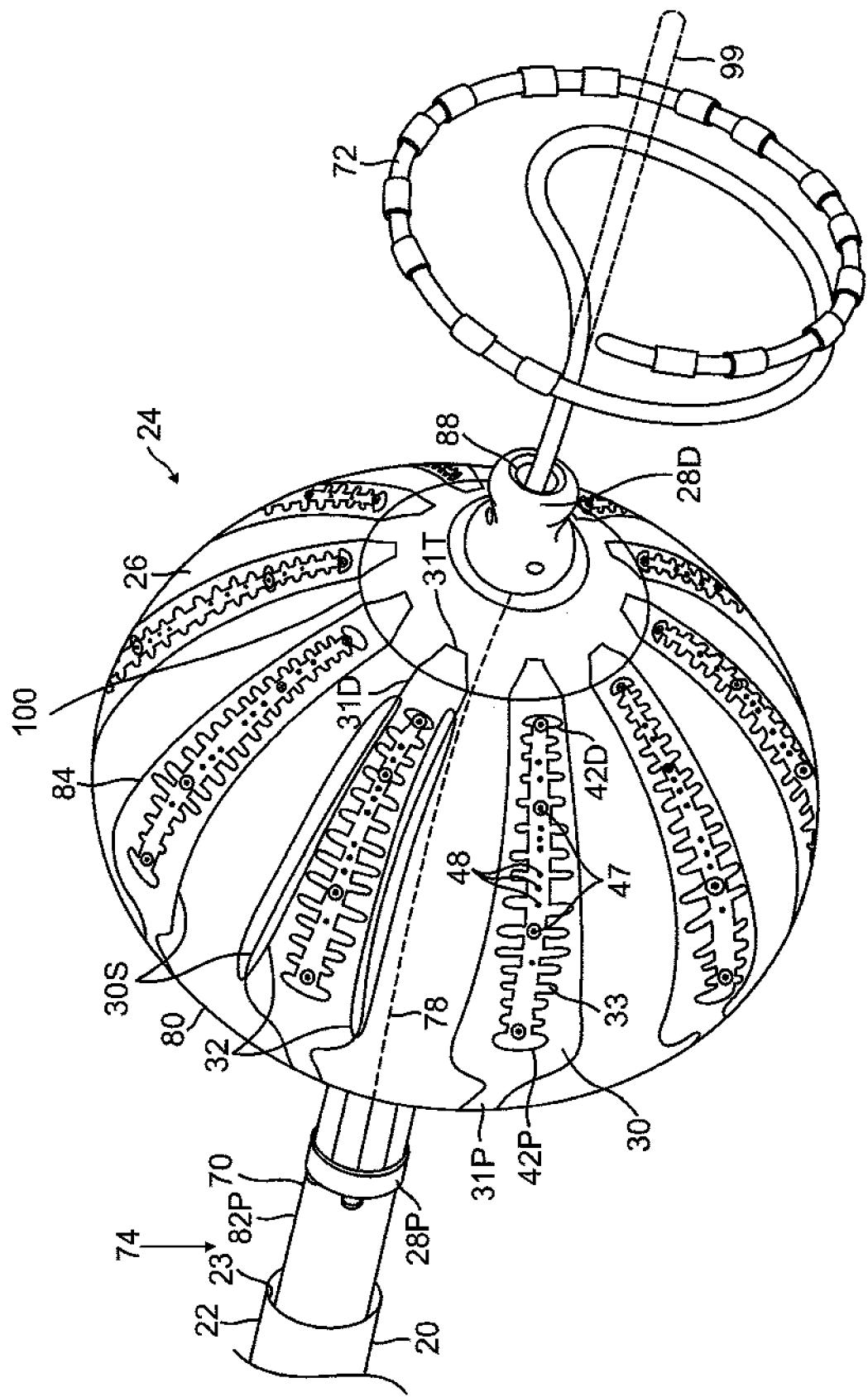
FIG. 3 depicts a perspective view of a distal end of the catheter of FIG. 2, reflecting the balloon as including a reinforcement comprising a reinforcement component.
Figure 4:
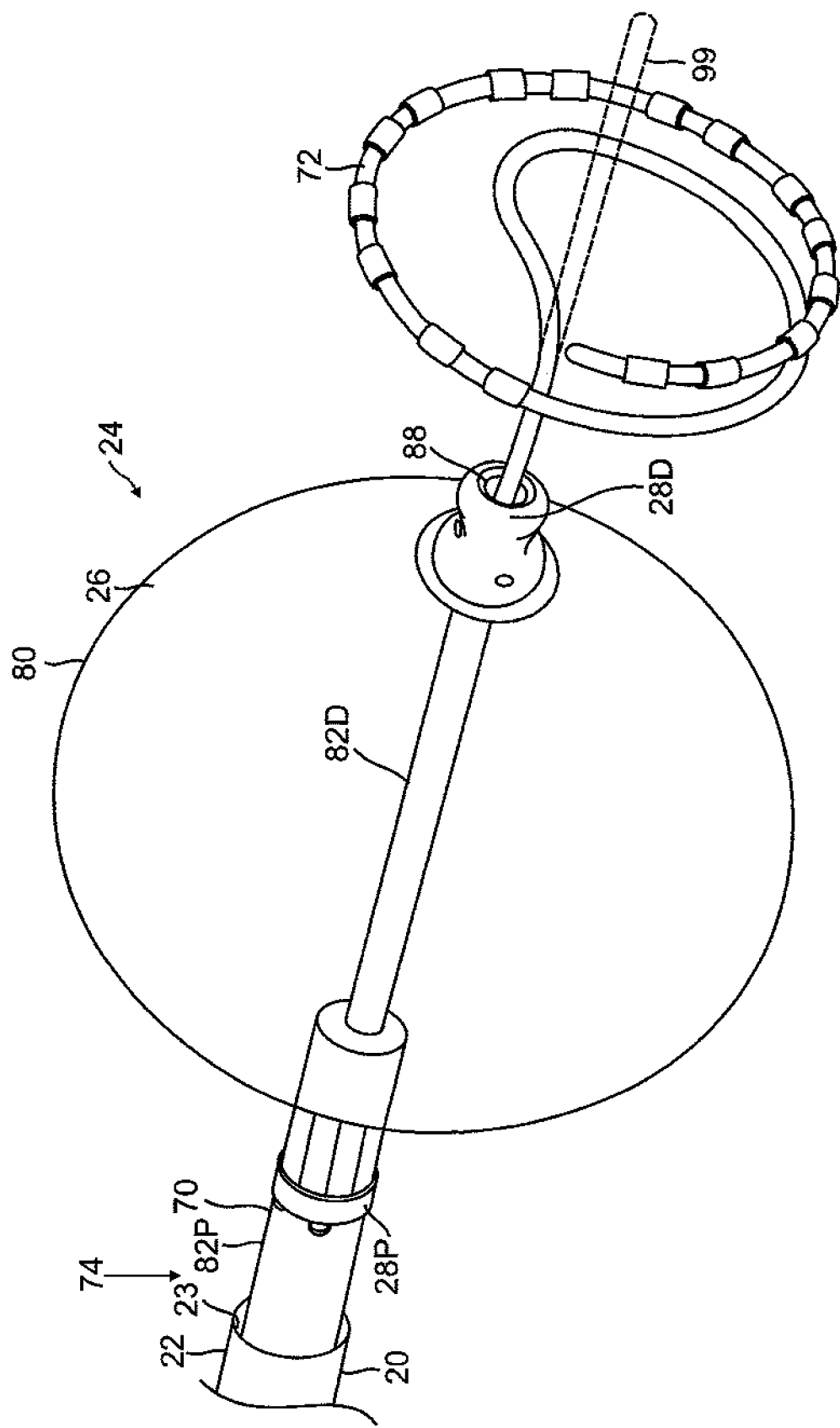
FIG. 4 depicts a perspective view of a distal end of the catheter of FIG. 2, reflecting structure of the catheter internal to the balloon.

FIG. 3 is a schematic perspective view of the diagnostic/therapeutic catheter 24 in an expandable configuration in the form of a balloon in its expanded configuration, according to an embodiment. The diagnostic/therapeutic catheter 24 is supported by a tubular shaft 70 having a proximal shaft portion 82P, a distal shaft portion 82D and a distal shaft end 88. As depicted in FIG. 4, which is similar to FIG. 3, but with external structures on balloon 80 hidden, distal or second shaft portion 82D is disposed at least partially within the proximal or first shaft portion 82P in a telescoping relationship therewith. The shaft 70 also includes a hollow central tube 74, which permits a catheter to pass therethrough and past the distal shaft end 88. The catheter may be a focal linear catheter or a lasso catheter 72, as illustrated. The lasso catheter 72 may be inserted into the pulmonary vein to position the diagnostic/therapeutic catheter 24 correctly with respect to the ostium prior to ablation of the ostium. The distal lasso portion of the catheter 72 is typically formed of shape-memory retentive material such as nitinol. It is understood that the diagnostic/therapeutic catheter 24 may also be used with a linear or focal catheter 99 (as shown in broken lines in FIG. 3) in the PV or elsewhere in the heart. The focal catheter 99 may include a force sensor at its distal tip. Suitable force sensing distal tips are disclosed in U.S. Pat. Nos. 8,357,152 and 10,688,278, the entire contents of which are incorporated by reference herein. Any catheter used in conjunction with the diagnostic/therapeutic catheter may have features and functions, including, for example, pressure sensing, ablation, diagnostic, e.g., navigation and pacing.

Figure 5:
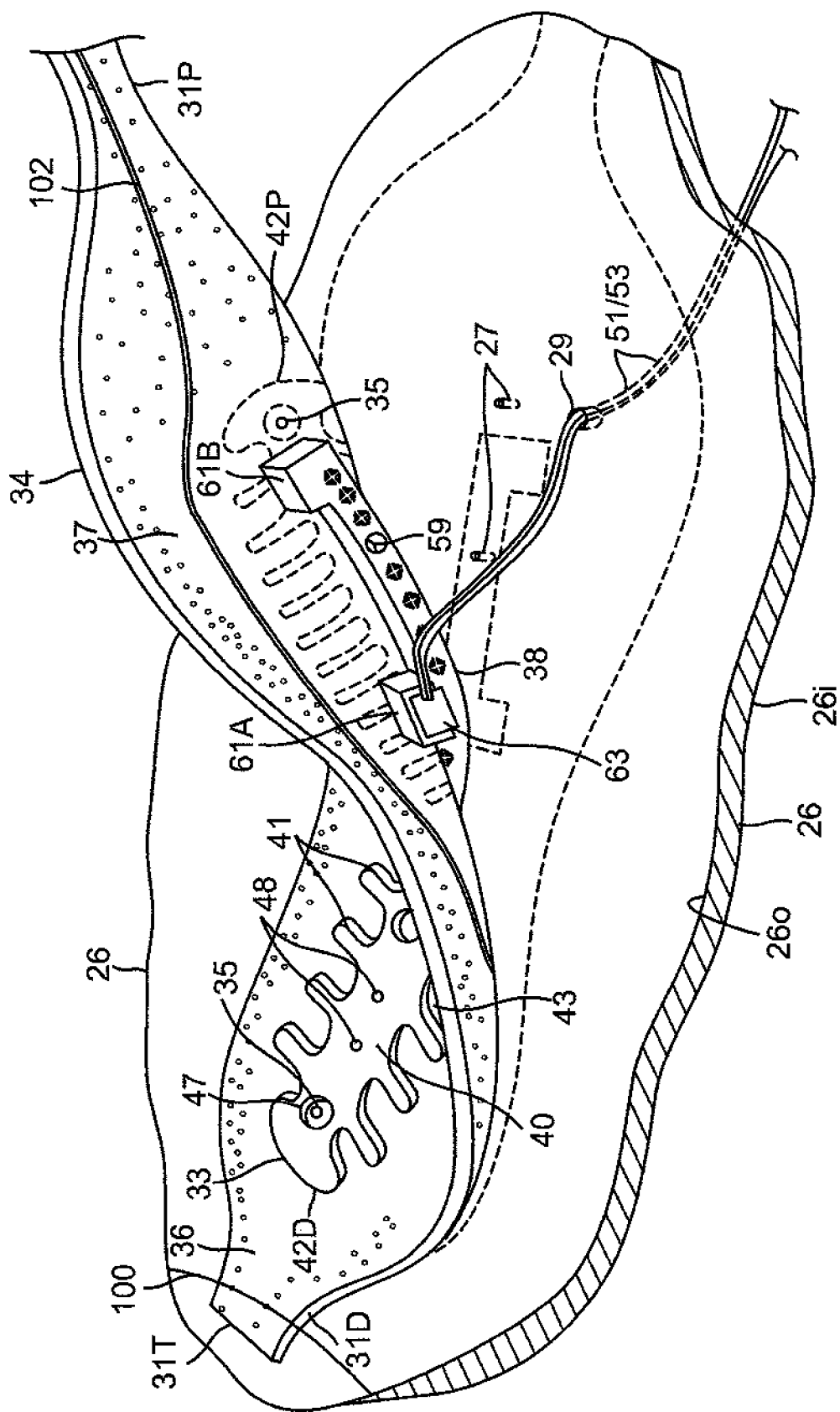
FIG. 5 depicts a perspective detail view of a flex circuit electrode assembly on the balloon of FIG. 3.

With further reference to FIG. 5, balloon 80 of the diagnostic/therapeutic catheter 24 comprises a membrane 26 of a bio-compatible material, for example, formed from a plastic such as polyethylene terephthalate (PET), polyurethane, Pellethane® or PEBAX®. Membrane 26 has an outer surface 26o and an inner surface 26i. A reinforcement comprising a reinforcement component 100 may additionally be provided about the distal portion of membrane 26, on outer surface 26o, such as the reinforcement component 100 described in U.S. patent application Ser. No. 16/432,392, published as U.S. Patent Application Publication No. 2020/0001054, the entire content of which is incorporated by reference herein. Membrane 26, and thus balloon 80, have a proximal end 87 and a distal end 89 at distal shaft end 88.

The shaft 70 and the distal shaft end 88 define a longitudinal axis 78 of the balloon 80. The balloon 80 is deployed, in a collapsed configuration, via the lumen 23 of the probe 20. A proximal end of membrane 26 of balloon 80 is attached to first or proximal shaft portion 82P and a distal end of membrane 26 of balloon 80 is attached to second or distal shaft portion 82D, proximate to distal shaft end 88. Balloon 80 may be expanded to an expanded configuration after exiting from the distal end 22 by moving distal shaft end 88 proximally to shorten the distance between the distal end 89 of balloon 80 and proximal end 87 of balloon 80, and thus increase the width of balloon 80, i.e., by telescoping distal shaft portion 82D proximally in the proximal shaft portion 82P. Passing irrigation fluid into balloon 80 may further expand balloon 80. Balloon 80 may be returned to its collapsed configuration by ceasing the irrigation and then moving distal shaft end 88 away from proximal end 87 to decrease the width of and extend the length of balloon 80, i.e., by telescoping distal shaft portion 82D distally in proximal shaft portion 82P. This telescopic motion between the first shaft portion and the second shaft portion may be controlled by knob 85 of control handle 83, shown in FIG. 2. Specifically, knob 85 may be rotated in a first direction to extend distal shaft portion 82D distally, and thus move distal shaft end 88 distally, whereas knob 85 may be rotated in the opposite direction to withdraw distal shaft portion 82D proximally, and thus move distal shaft end 88 proximally. Knob 85 may further include locking features, such as detents, to maintain distal shaft end at its most proximal location and at its most distal location. Such locking features help prevent balloon 80 from collapsing somewhat out of its expanded configuration during ablation and from expanding somewhat out if its collapsed configuration during withdrawal into lumen 23 of probe 20. Further description concerning transitioning the balloon between a collapsed configuration and an expanded configuration is set forth in U.S. patent application Ser. No. 15/827,111, published as U.S. Patent Application Publication No. 2018/0161093. The entire content of this application is incorporated by reference herein in its entirety.

The membrane 26 supports and carries a combined electrode and temperature sensing member which is constructed as a multi-layer flexible circuit electrode assembly 84. The "flex circuit electrode assembly" 84 may have many different geometric configurations. In the illustrated embodiment, the flex circuit electrode assembly 84 has a plurality of radiating substrates or strips 30. The substrates 30 are evenly distributed about outer membrane surface 26o of balloon 80. Each substrate has wider proximal portion that gradually tapers to a narrower distal portion.

Each substrate 30 has a proximal tail 31P proximal to the wider proximal portion and a distal tail 31D distal of the narrower distal portion. As described below, distal tail portion 31D may terminate at distal tip 31T, proximal of distal shaft end 88, or may extend up to distal shaft end 88 to be secured thereunder. Substrate 30 may be bonded to membrane 26 with an adhesive, such as an epoxy. Some adhesive may be disposed between inner surface 37 of substrate 30 and membrane 26. Additionally, an adhesive margin 32 may be overlaid about edges of substrate 30, such as side edges 30S, to help further minimize the likelihood delamination of substrate 30 from membrane 26. A portion of adhesive margin 32 adheres directly to the top of membrane 26 while the rest of the adhesive of adhesive margin 32 adheres directly to outer surface 36 of substrate 30. Adhesive margin 32 may be applied as beads, two or more discrete linear segments, or as a single linear segment that extends over most or all of each side edge 30S. Preferably, the overlap portion 32O of adhesive margin 32 that adheres directly to the top of membrane 26 extends outwardly form side edges 30S by a distance D1 of between about 0.3 millimeters and about 0.6 millimeters, e.g., about 0.45 millimeters. Such is reflected in FIG. 12B.

The flex circuit electrode assembly 84 is described with respect to one of its substrates 30 as shown in FIG. 5, although it is understood that the following description may apply to each substrate of the assembly. The flex circuit electrode assembly 84 includes a flexible and resilient sheet substrate 34, constructed of suitable bio-compatible materials, for example, polyimide. In some embodiments, the sheet substrate 34 has a greater heat resistance (or a higher melting temperature) compared to that of the balloon membrane 26. In some embodiments, the substrate 34 is constructed of a thermoset material having a decomposition temperature that is higher than the melting temperature of the balloon membrane 26 by approximately 100 degrees Celsius or more.

The substrate 34 is formed with one or more irrigation pores or apertures 35 that are in alignment with the irrigation apertures 27 of the balloon member 26 so that fluid passing through the irrigation apertures 27 and 35 can pass to the ablation site on the ostium. Substrate 34 may be cut to shape by, and the irrigation pores 35 formed by, any suitable manufacturing technique, such as laser cutting.

The substrate 34 has a first or outer surface 36 facing away from the balloon membrane 26, and a second or inner surface 37 facing the balloon membrane 26. On its outer surface 36, the substrate 34 supports and carries the contact electrodes 33 adapted for tissue contact with the ostium. On its inner surface 37, the substrate 34 supports and carries a wiring electrode 38. The contact electrode 33 delivers RF energy to the ostium during ablation or is connected to a thermocouple junction for temperature sensing of the ostium. In the illustrated embodiment, the contact electrode 33 has a longitudinally elongated portion 40 and a plurality of thin transversal linear portions or fingers 41 extending generally perpendicularly from each lateral side of the elongated portion 40 between enlarged proximal and distal ends 42P and 42D, generally evenly spaced therebetween. The elongated portion 40 has a greater width and each of the fingers has a generally uniform lesser width. Accordingly, the configuration or trace of the contact electrode 33 may resemble a "fishbone" but it should be noted that the invention is not limited to such configuration. In contrast to an area or "patch" ablation electrode, the fingers 41 of the contact electrode 33 advantageously increase the circumferential or equatorial contact surface of the contact electrode 33 with the ostium while void regions 43 between adjacent fingers 41 advantageously allow the balloon 80 to collapse inwardly or expand radially as needed at locations along its equator. In the illustrated embodiment, the fingers 41 have different lengths, some being longer, others being shorter. For example, the plurality of fingers includes a distal finger, a proximal finger and fingers therebetween, where each of the fingers in between has a shorter adjacent finger. For example, each finger has a length different from its distal or proximal immediately adjacent neighboring finger(s) such that the length of each finger generally follows the tapered configuration of each substrate 30. In the illustrated embodiment, there are 22 fingers extending across (past each lateral side of) the elongated portion 40, with the longest finger being the third finger from the enlarged proximal end 42P. In some embodiments, the contact electrode 33 includes gold with a seed layer between the gold and the membrane 26. The seed layer may include titanium, tungsten, palladium, silver, or combinations thereof.

Formed within the contact electrode 33 are one or more exclusion zones 47, each surrounding an irrigation aperture 35 formed in the substrate 34. The exclusion zones 47 are voids purposefully formed in the contact electrode 33, as explained in detail further below, so as to avoid damage to the contact electrode 33 during construction of the electrode assembly 84 in accommodating the irrigation apertures 35 at their locations and in their function.

Also formed in the contact electrode 33 are one or more conductive blind vias 48 which are conductive or metallic formations that extend through through-holes in the substrate 34 and are configured as electrical conduits connecting the contact electrode 33 on the outer surface 36 and the wiring electrode 38 on the inner surface 37. It is understood that "conductive" is used herein interchangeably with "metallic" in all relevant instances.

In the illustrated embodiment, the contact electrode 33 measures longitudinally between about 0.1 inch and 1.0 inch, and preferably between about 0.5 inch and 0.7 inch, and more preferably about 0.57 inch, and has four exclusion zones 47 and nine blind vias 48.

On the inner surface 37 of the substrate 34, the wiring electrode 38 is generally configured as an elongated body generally similar in shape and size to the elongated portion 40 of the contact electrode 33. The wiring electrode 38 loosely resembles a "spine" and also functions as a spine in terms of providing a predetermined degree of longitudinal rigidity to each substrate 30 of the electrode assembly 84. The wiring electrode 38 is positioned such that each of the blind vias 48 is in conductive contact with both the contact electrode 33 and the wiring electrode 38. In the illustrated embodiment, the two electrodes 33 and 38 are in longitudinal alignment with other, with all nine blind vias 48 in conductive contact with both electrodes 33 and 38. In some embodiments, the wiring electrode 38 has an inner portion of copper and an outer portion of gold.

The wiring electrode 38 is also formed with its exclusion zones 59 around the irrigation apertures 35 in the substrate 34. The wiring electrode 38 is further formed with solder pad portions, at least one active 61A, and there may be one or more inactive solder pad portions 61B. The solder pad portions 61A and 61B are extensions from a lateral side of the elongated body of the wiring electrode 38. In the illustrated embodiment, an active solder pad portion 61A is formed at about a mid-location along the elongated body, and a respective inactive solder pad portion 61B is provided at each of the enlarged distal end 42D and the enlarged proximal end 42P.

Attached, e.g., by a solder weld 63, to the active solder pad portion 61A are the wire pair, e.g., a constantan wire 51 and a copper wire 53. The copper wire 53 provides a lead wire to the wiring electrode 33, and the copper wire 53 and the constantan wire 51 provide a thermocouple whose junction is at solder weld 63. The wire pair 51/53 are passed through a through-hole 29 formed in the membrane 26. It is understood that, in other embodiments in the absence of the through-hole 29, the wire pair 51/53 may run between the membrane 26 and the substrate 34 and further proximally between the membrane 26 and the proximal tail 31P until the wire pair 51/53 enters the tubular shaft 70 via another through-hole (not shown) formed in the tubular shaft sidewall closer to the proximal ring 28P.

The flex circuit electrode assembly 84, including the substrates 30 and the tails 31P and 31D, is affixed to the balloon membrane 26 such that the outer surface 36 of the substrate 34 is exposed and the inner surface 37 of the substrate 34 is affixed to the balloon membrane 26, with the wiring electrode 38 and wire pair 51/53 sandwiched between the substrate 34 and the balloon membrane 26. The irrigation apertures 35 in the substrate 34 are aligned with the irrigation apertures 27 in the balloon membrane 26. The exclusion zones 59 in the wiring electrode 38 and the exclusion zones 47 in the contact electrode 33 are concentrically aligned with each other, as well as with the irrigation apertures 27 and 35 in balloon 26 and substrate 34, respectively.

Further details on constructing a diagnostic/therapeutic catheter in accordance with the foregoing disclosure may be found in U.S. patent application Ser. No. 15/360,966, published as U.S. Patent Application Publication No. 2017/0312022. The entire content of this application is incorporated by reference herein in its entirety.

Improved Robustness

Through ongoing research and product development efforts concerning the subject matter described above, Applicant has determined that balloon 80 must be able to withstand multiple cycles of being deployed from lumen 23 of probe 20 in a collapsed configuration, expanded to an expanded configuration, returned to the collapsed configuration, and withdrawn into lumen 23 of probe 20. The number of cycles may be from about five to about twenty. Thus, the connection between substrate 30 and membrane 26 of balloon 80, and the overall integrity of the assembled balloon, must withstand at least five to twenty fatigue cycles.

Applicant has observed that users of prior iterations of diagnostic/therapeutic catheter 24 sometimes do not lock knob 85 after returning balloon 80 to its collapsed configuration and before attempting to withdraw it into lumen 23 of probe 20. When knob 85 is locked and balloon 80 is in the collapsed configuration, balloon 80 is taut and the width of balloon 80 is less than the inner diameter of lumen 23. However, when knob 85 is not locked, balloon 80 may not be fully taut such that it may expand somewhat, causing the width of balloon 80 to approach or surpass the internal diameter of lumen 23. This can cause balloon 80 to bunch up on itself as it is withdrawn into lumen 23. In turn, this can cause balloon 80 to stick in lumen 23, which increases the load necessary to move balloon 80 in lumen 23 and the resulting shear stresses on distal tails 31D. These increased forces and stresses increase the likelihood of device malfunction. Applicant has thus been seeking solutions.

Figure 12A:
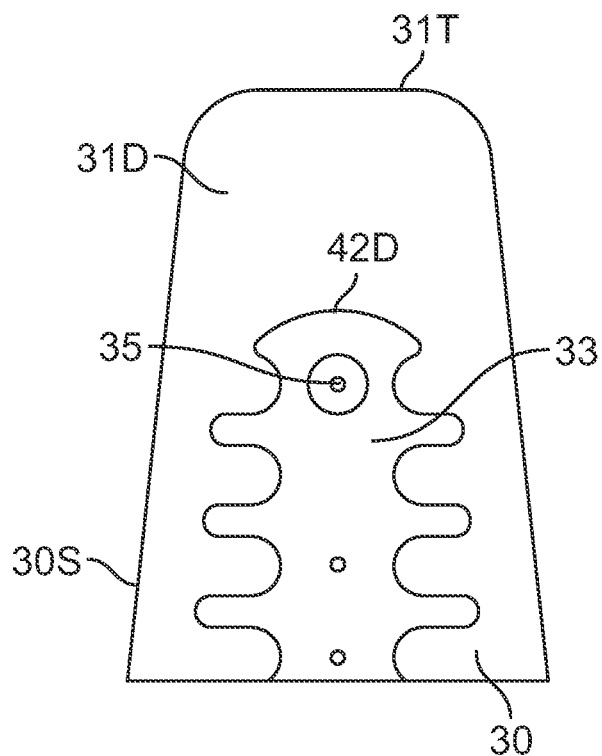
FIG. 12A depicts a detail view of a distal end of a substrate that is disposed on the balloon of FIG. 3.

Applicant has identified some solutions, embodiments for two of which are described herein. An exemplary embodiment of the first solution is reflected in FIGS. 3-5, where distal tail 31D of substrate 30 terminates at tip 31T. Tip 31T and a portion of distal tail 31D are sandwiched between membrane 26 and a reinforcement comprising a reinforcement component 100. With reference to FIG. 12A, for a balloon 80 that is to be provided in its collapsed configuration through a probe 20 having a 13.5 french internal diameter (e.g., the DESTINO™ Twist Guiding Sheath by Oscor, Inc), the distance from the center of the distal-most irrigation pore 35 to tip 31T is between about 1 millimeter and about 3 millimeters, e.g., about 2 millimeters, as measured along the surface of substrate 30.

Figure 6:
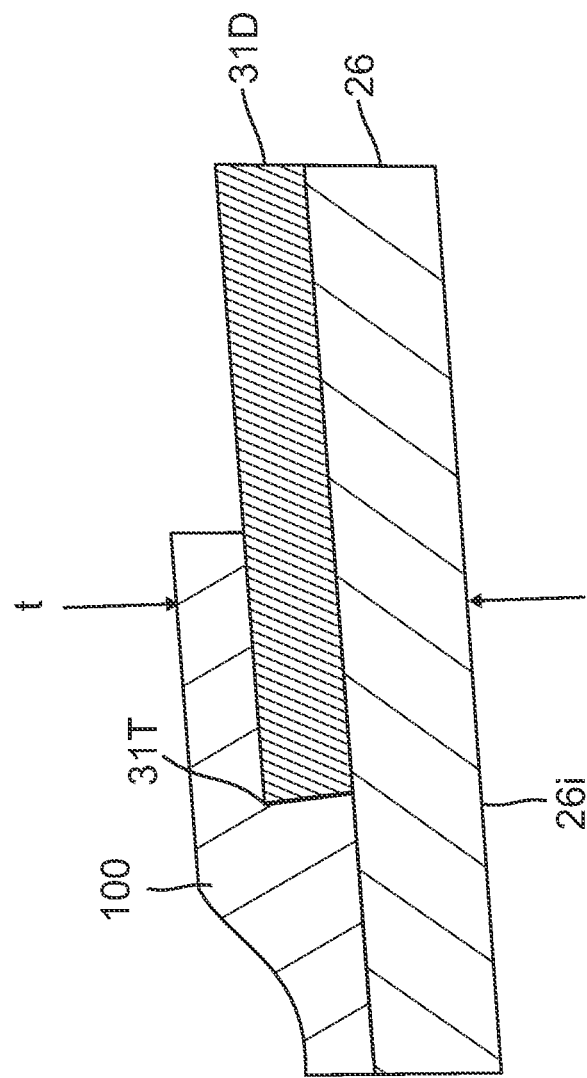
FIG. 6 depicts a cross-section view of a distal segment of the balloon.
Figure 7:
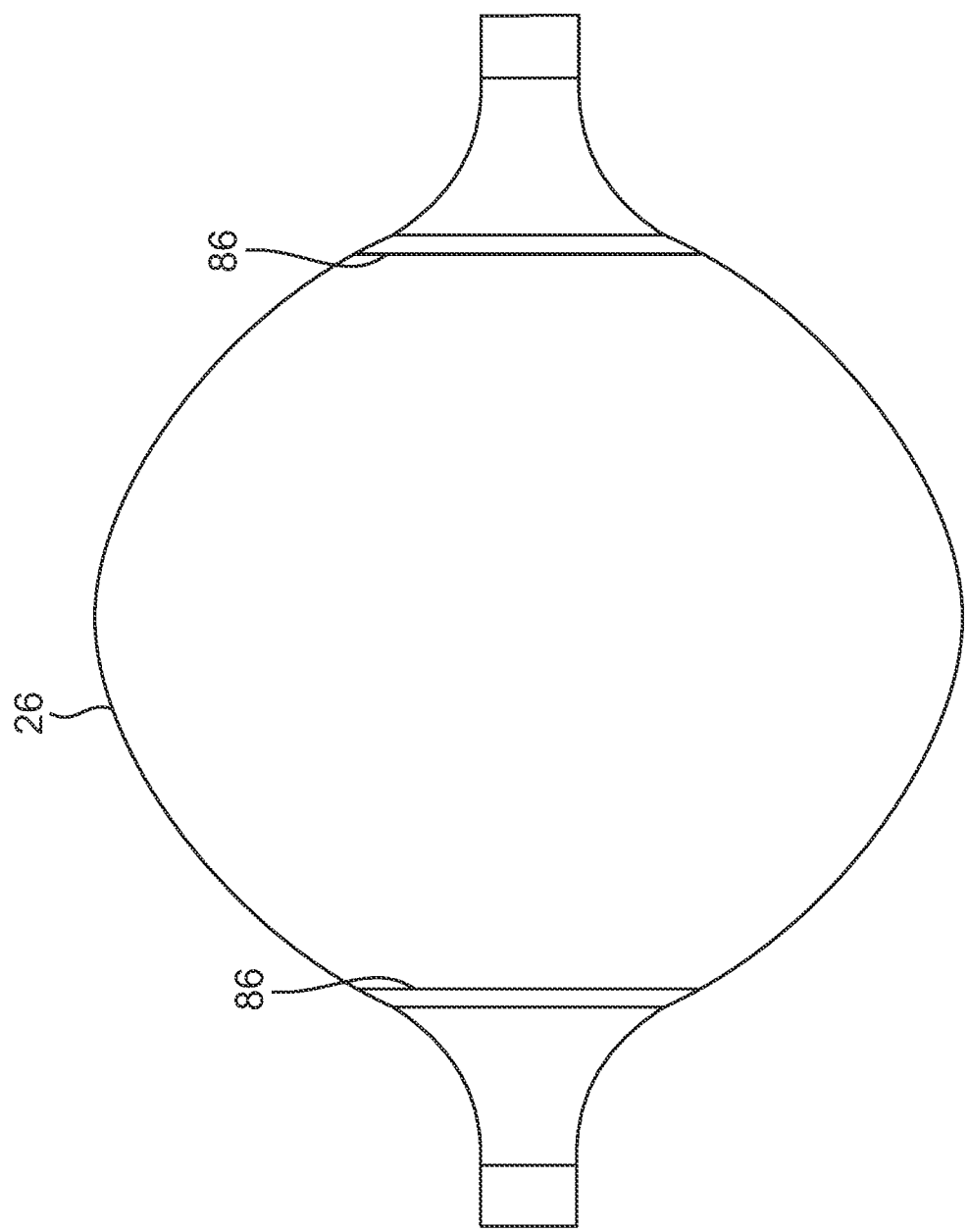
FIG. 7 depicts a side view of an unassembled balloon component.

Reinforcement component 100 conforms to a distal portion of membrane 26. For example, reinforcement component 100 may include a portion of an unassembled membrane 26, i.e., a membrane 26 that has not been assembled to any other components of catheter 24, such as substrates 30. That is, an unassembled instance of membrane 26 may have a portion separated therefrom by cutting it along one of the lines 86 as seen in FIG. 6. In embodiments where membrane 26 is symmetric about a center line, two portions of membrane 26 may be removed to create two reinforcement components 100. In embodiments where membrane 26 is asymmetric about a center line, the distal portion thereof may be used as reinforcement component 100 over distal tips 31T and respective adjacent portions of distal tails 31D.

Reinforcement component 100 may be adhered to membrane 26 via e.g., epoxy, or mechanical or thermal fusion. In this configuration reinforcement component 100 may absorb stresses caused by expanding and collapsing balloon 80 while also maintaining tip 31T against membrane 26, thereby reducing shear stresses on distal tail 31D. Moreover, the number of components and overall thickness of the assembly is minimized in the region between tip 31T and distal shaft end 88 as compared to prior iterations of catheter 24, e.g., as set forth in U.S. patent application Ser. No. 16/432,392, published as U.S. Patent Application Publication No. 2020/0001054, where distal tails 31D extended to distal shaft end 88 and were attached thereto by being tucked under distal cap 28D. With that design for a diagnostic/therapeutic catheter 24 having a balloon 80 that is to be provided in its collapsed configuration through a probe 20 having a 13.5 french internal diameter (e.g., the DESTINO™ Twist Guiding Sheath by Oscor, Inc), the overall thickness in the distal region of balloon 80 is about 0.012 inches. However, in the current design, where the only balloon materials between distal tip 31T and cap 28D are membrane 26, reinforcement component 100, and adhesive, the overall thickness t in a region of balloon 80 as measured from inner membrane surface 26i, through a distal tip 31T, and to an outer surface of reinforcement component 100 is about 0.0075 inches. Such is reflected in FIG. 6. This reduced thickness enables balloon 80, even when its width is greater than that of its collapsed configuration, to be withdrawn into lumen 23 with a minimal likelihood of distal tails 31D breaking or delaminating from membrane 26. That is, instead of the inner surfaces and tip of probe 20 interfering with the passage of balloon 80 therethrough, and thus causing friction and shear stresses of a magnitude that leads to malfunction, the tip of probe 20 helps guide the balloon into lumen 23. Further, because the thickness of balloon 80 in the distal region has been minimized such that the inner surfaces of lumen 23 do not squeeze balloon 80 and cause it to bunch up, friction forces are minimized and shear stresses sufficient to cause device malfunction are not generated.

To further assist in minimizing prospective delamination of substrates 30, a reinforcement filament 102 (FIG. 5) may be attached to substrate 30. Reinforcement filament 102 may extend along a portion of substrate 30, or along the entirety thereof, e.g., from a proximal tip of proximal tail 31P to distal tip 31T. As such, where balloon 80 includes ten substrates 30, ten reinforcement filaments 102 may also be provided, one on each of the ten substrates. The reinforcement filaments may be attached to substrates 30 by any suitable method, e.g., with an adhesive.

Preferably, each reinforcement filament 102 may have a form of a yarn, and when assembled take the shape of a roughly rectangular cross section having a thickness between about 0.0005 inches and 0.005 inches. The yarn may be fabricated from an ultra-high molecular weight polymer or a liquid-crystal polymer, e.g., VECTRAN™, manufactured by Kuraray. So long as the thickness of the yarn is less than the thickness of electrode 33, it may be disposed on a top surface of substrate 30, i.e., adjacent to electrode 33, such that it would not contact exterior surface 26 of balloon 80. However, if the thickness of the yarn is greater than the thickness of electrode 33, such that the yarn might interfere with the electrode's ability to conform to patient tissue, the yarn should be disposed on a bottom surface of the substrate, such that it would also be disposed directly against exterior surface 26 of balloon 80. Such is the embodiment reflected in FIG. 5. Accordingly, a tip of the reinforcement filament 102 that terminates at distal tail 31T would be also be sandwiched between reinforcement component 100 and membrane 26. Reinforcement filament 102 does not extend beyond distal tail 31T, and thus does not increase the overall thickness of balloon 80 in the region between distal tail 31T and cap 28D.

Figure 8:
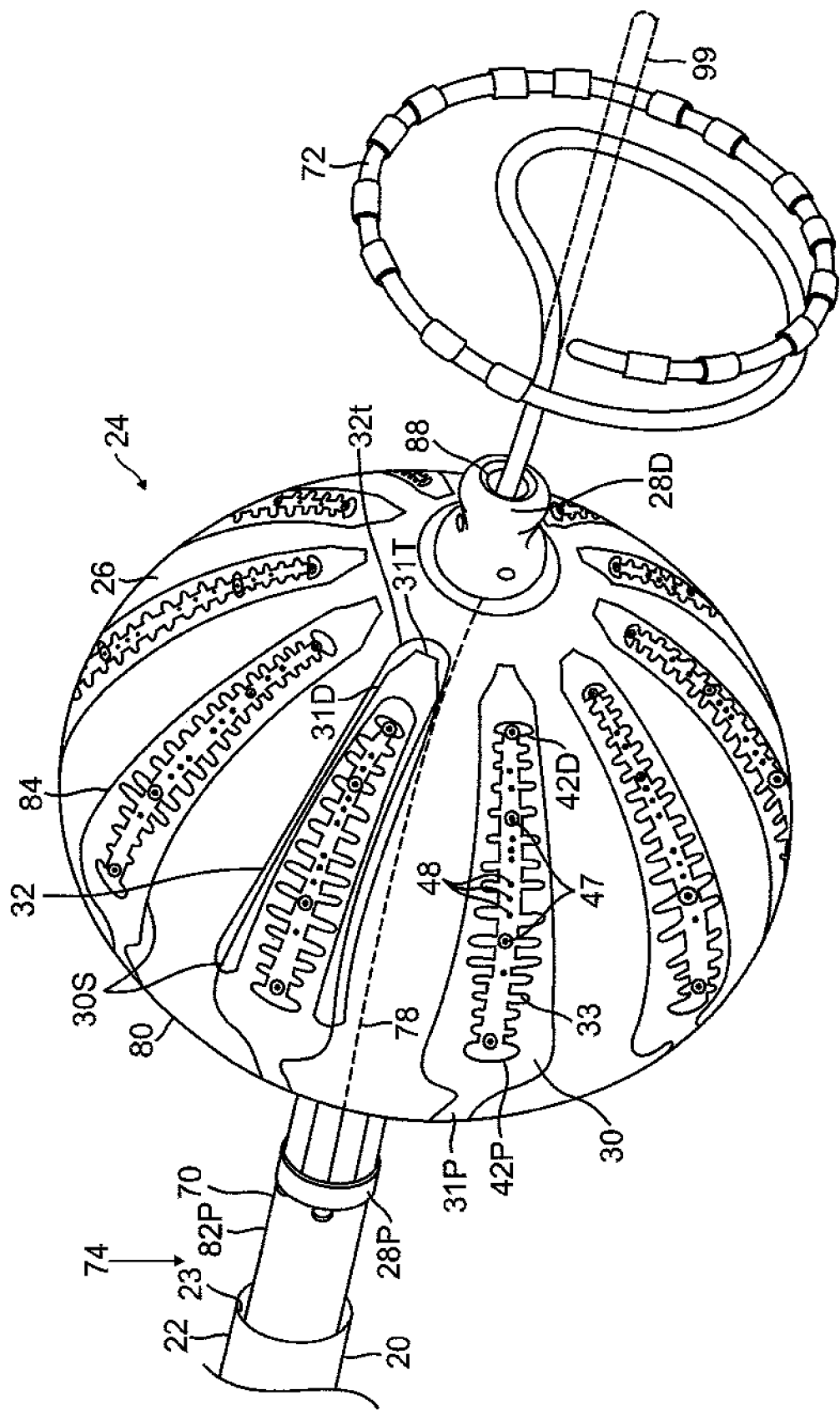
FIG. 8 depicts a perspective view of a distal end of the catheter of FIG. 2, reflecting the balloon as including a reinforcement comprising an adhesive margin tip.
Figure 12B:
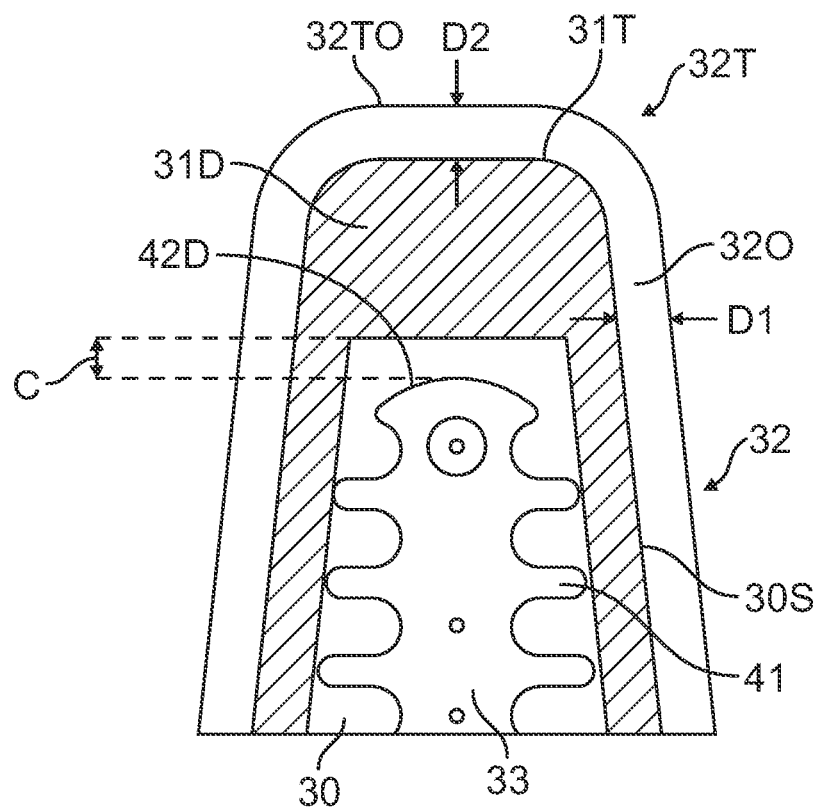
FIG. 12B depicts a detail view of a distal end of a substrate that is disposed on the balloon of FIG. 8, and bonding therebetween.

In an alternative embodiment of the first solution, reinforcement component 100 may be excluded. Instead, distal tip 31T is adhered directly to membrane 26. Such may be accomplished by providing the adhesive on inner surface 37 in the region of distal tip 31T, and also extending adhesive margin 32 around distal tip 31T, reflected in FIG. 8 as adhesive-margin tip 32T. As noted above with reference to FIG. 12B, the overlap portion 32O of adhesive margin 32 that adheres directly to the top of membrane 26 extends outwardly form side edges 30S by a distance D1 of between about 0.3 millimeters and about 0.6 millimeters, e.g., about 0.45 millimeters. Similarly, an overlap portion 32TO of adhesive-margin tip 32T that adheres directly to the top of membrane 26 extends outwardly from tip 31T by a distance D2 of between about 0.3 millimeters and about 0.6 millimeters, e.g., about 0.45 millimeters. For example, the distance that these overlap portions 32O and 32TO extend away from substrate 30 may be equal. Additionally, no portion of adhesive margin 32 or adhesive-margin tip 32T should cover any of electrode 33 because such could interfere with the ability of contact electrode 33 to ablate tissue. However, the strength of the bond between substrate 30 and membrane 26 is maximized when a clearance C between the adhesive and electrode 33 is minimized. For example, the clearance may be between about zero millimeters and about 0.5 millimeters. As depicted in FIG. 12B, adhesive margin 32 abuts fingers 41 of electrode 33 for a clearance of C=0 while adhesive-margin tip is spaced by C≤5 millimeters from distal end 42D of electrode 33. In this embodiment, adhesive margin tip 32T may be considered a reinforcement that provides a similar function to reinforcement component 100.

Figure 9:
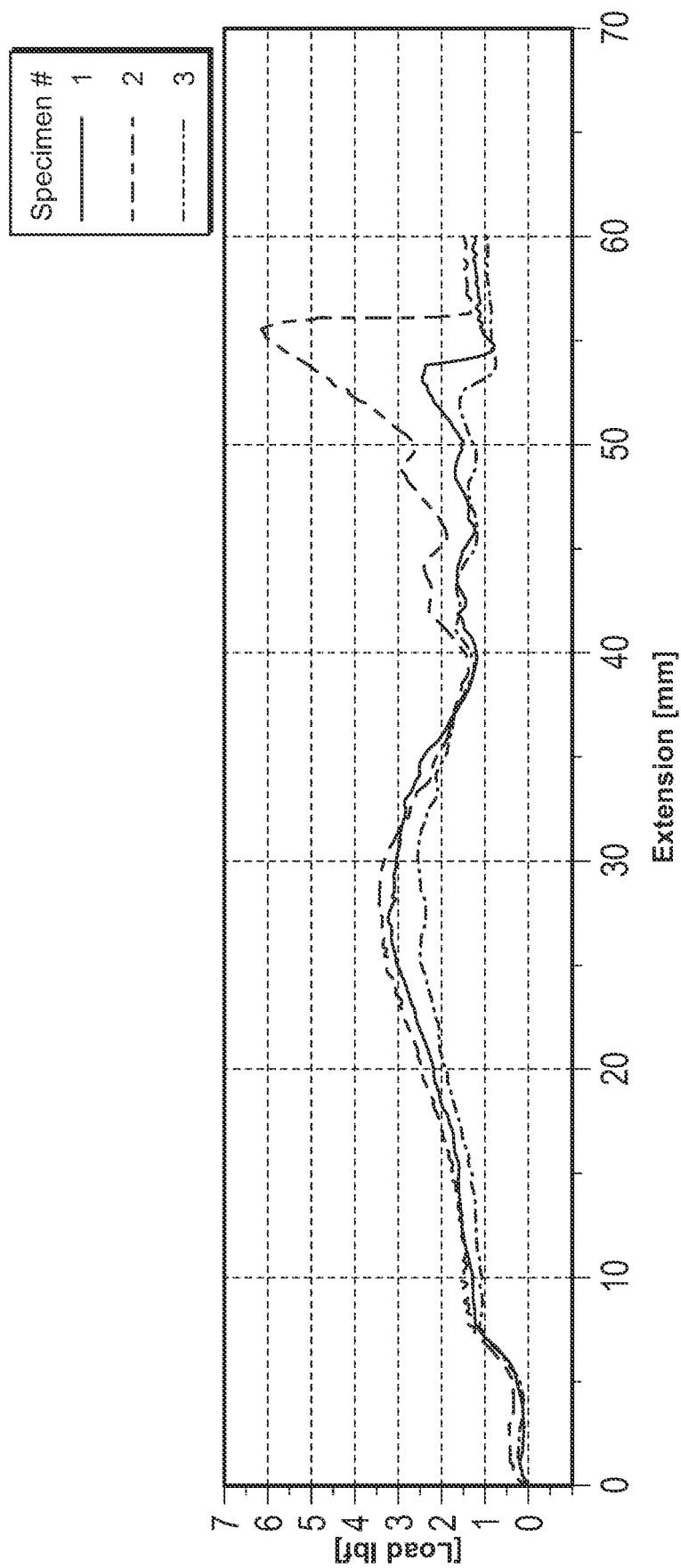
FIG. 9 depicts graph of force data relating to balloon movement.

FIG. 9 reflects a graph of force data collected as balloon 80 is withdrawn into probe 20. Balloon 80 begins its travel entirely outside of probe 20 and ends its travel entirely inside probe 20. Specimens 1 and 2 each correspond to balloon 80 being placed in its collapsed configuration before it is withdrawn into probe 20. Specimen 3 corresponds to balloon 80 being placed into a not-entirely collapsed configuration, e.g., in accordance with not locking knob 85 as described above. As can be seen, the maximum force measured for specimen 3 is about 6 lbf. This maximum force occurs when the not entirely collapsed balloon is withdrawn into probe 20. As can be seen for specimens 1 and 2, the force does not noticeably increase at this same positioning because the balloon in the collapsed configuration has ample clearance to enter probe 20. Applicant reports, however, that for the design reflected in U.S. patent application Ser. No. 16/432,392, published as U.S. Patent Application Publication No. 2020/0001054, the force required to withdraw a not entirely collapsed balloon into probe 20 is often greater than 25 lbf, over four times as much as for specimen 3. Accordingly, the force reduction enabled by the current design evidences that the current design can better accommodate withdrawal of balloon 80 into probe 20, even when balloon 80 is not entirely collapsed before withdrawal into probe 20.

Figure 10:
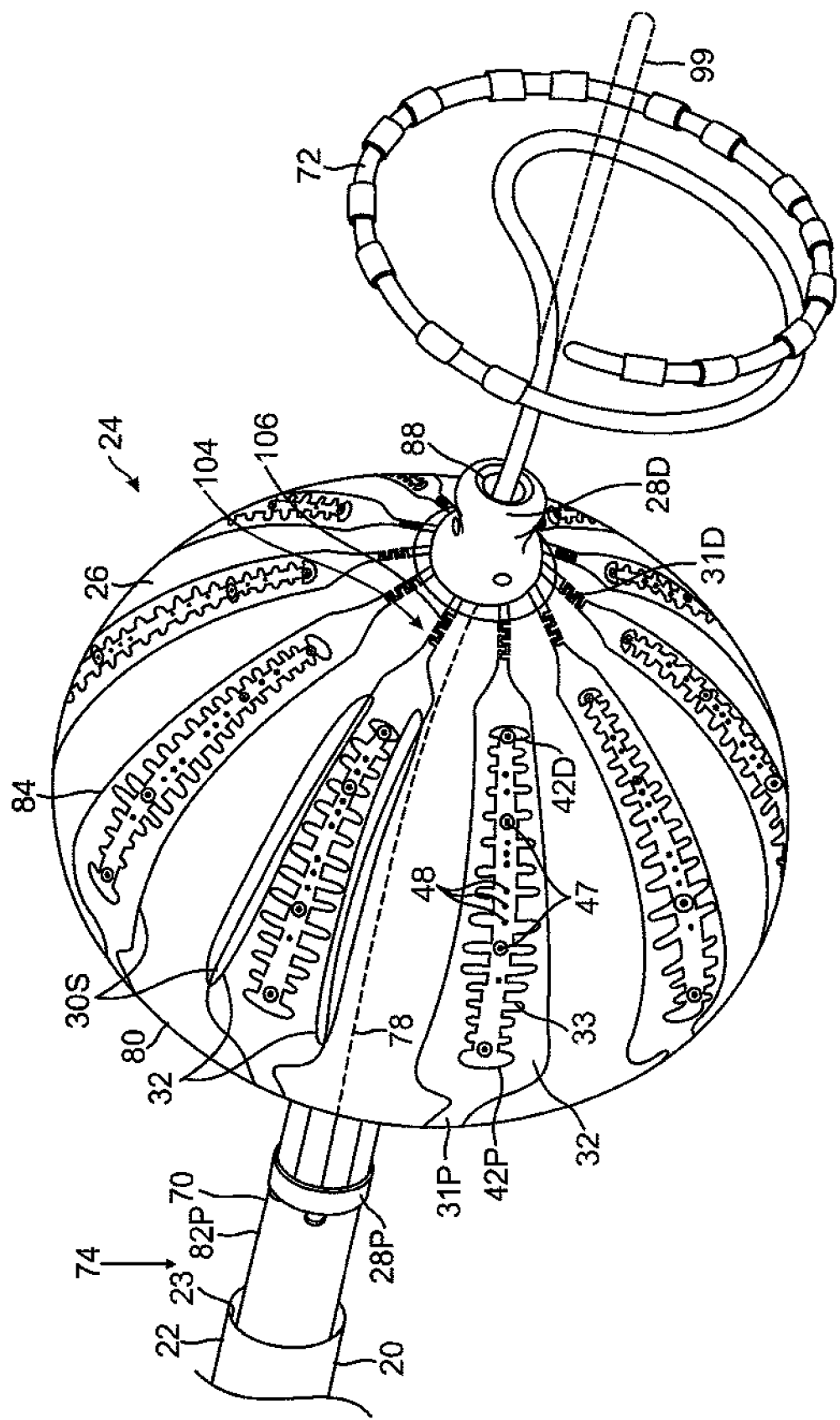
FIG. 10 depicts a perspective view of a distal end of the catheter of FIG. 2, reflecting the balloon as including a stress relief.

An exemplary embodiment of a second solution is reflected in FIG. 10. In this embodiment, distal tail 31D extends to distal shaft end 88 where it is tucked under distal ring or cap 28D. Distal tail 31D includes a distal-tail portion 104 having a serpentine form 106. Serpentine form 106 provides a stress relief to distal tails 31D by increasing the ability of distal-tail portion 104 to conform to the shape of balloon 80 and accommodate generated shear stresses whenever balloon 80 is being collapsed, expanded, withdrawn into lumen 23, or extended out of lumen 23. Serpentine form 106 may be formed as part of the fabrication process of substrate 30, e.g., during the formation of substrate 34. For example, serpentine form 106 may be created in substrate 34 as substrate 34 is being cut to shape, which, as noted above, may be performed by any suitable manufacturing technique, such as laser cutting.

Reinforcement filament 102, described above, may also be included as a feature of substrate 30 when substrate 30 includes serpentine form 106. Filament 102 may extend from a proximal position on substrate 30 up to the proximal end of serpentine form 106. Alternatively, reinforcement filament 102 may also be provided as having a serpentine form, such that it can extend to distal shaft end 88 commensurate with the entirety of distal tail 31D, as seen in FIG. 11A.

Serpentine form 106 may be optimized based on the forces it is subject to as balloon 80 is transitioned from the collapsed configuration to the expanded configuration and back to the collapsed configuration again, as well as the number of such cycles it is subject to. For example, as reflected in FIG. 11A, the serpentine pattern may comprise a square wave 106*a*, which may also have rounded corners, whereas, as reflected in FIG. 11B, the serpentine pattern may comprise a curved wave 106*b*. The serpentine pattern may also extend over about 3 to about 10 periods. For example, square-wave pattern 106*a* is reflected as comprising nearly four periods, while curved-wave pattern 106*b* is reflected as having five periods. Additionally, as depicted in FIG. 11A, the width of serpentine form 106*a* is denoted by w and the width of the distal tail is denoted by W. The width w of serpentine form 106*a* may be between about ⅒ and about ½ of the width W of distal tail 31D.

The choice of which of the various embodiments of the two solutions described above to improve the robustness of balloon 80, particularly in its distal region, depend on various factors, such as the overall size of balloon 80, the size of the lumen 23 through which balloon 80 travels, and the number of fatigue cycles to which balloon 80 will be subject.

Any of the examples or embodiments described herein may include various other features in addition to or in lieu of those described above. The teachings, expressions, embodiments, examples, etc., described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A catheter balloon, comprising:
a membrane including a proximal end and a distal end;
ten substrates disposed about the membrane, each of the ten substrates including an outer surface, an inner surface, and a respective tail terminating at a respective distal tip disposed proximal to the distal end of the membrane and spaced from the distal end of the membrane;
ten contact electrodes disposed on the outer surface of each of the ten substrates, such that a single contact electrode is disposed on a respective substrate and such that a distal end of each single contact electrode is disposed closer to the proximal end of the membrane than the respective distal tip of the respective substrate;
an adhesive disposed between the inner surface of each of the ten substrates and the membrane; and
a reinforcement disposed atop each respective distal tip and an adjacent portion of the membrane that is disposed distal of the respective distal tip, the reinforcement not being disposed atop any portion of the ten contact electrodes, such that a thickness of the catheter balloon as measured from an inner surface of the membrane, through a respective distal tip, and to an outer surface of the reinforcement is about 0.0075 inches.

2. The catheter balloon of claim 1, in which the ten substrates each include a plurality of irrigation pores including a distal irrigation pore, and a distance between each respective distal tip and each respective distal irrigation pore is between about 1 millimeter and about 3 millimeters.

3. The catheter balloon of claim 1, in which the ten substrates each include side edges and the catheter balloon further comprises an adhesive margin disposed atop the side edges and the membrane.

4. The catheter balloon of claim 3, in which the reinforcement comprises a portion of an unassembled membrane.

5. The catheter balloon of claim 3, in which the reinforcement comprises an adhesive-margin tip.

6. The catheter balloon of claim 5, in which a portion of the adhesive-margin tip contacts the membrane and the portion of the adhesive-margin tip that contacts the membrane extends from the respective distal tip by between about 0.3 millimeters and about 0.6 millimeters.

7. A catheter, comprising:
   a probe having a lumen with an inner diameter of about 13.5 french;
   a shaft disposed in the lumen, the shaft having a first shaft portion and a second shaft portion partially disposed within the first shaft portion in a telescoping relationship with the first shaft portion;
   a catheter balloon disposed in the lumen, the catheter balloon having a membrane including a proximal end and a distal end, the proximal end connected to the first shaft portion and the distal end connected to the second shaft portion;
   ten substrates disposed about the membrane, each of the ten substrates including an outer surface, an inner surface, and a respective tail terminating at a respective distal tip disposed proximal to the distal end of the membrane and spaced from the distal end of the membrane;
   ten contact electrodes disposed on the outer surface of each of the ten substrates, such that a single contact electrode is disposed on a respective substrate and such that a distal end of each single contact electrode is disposed closer to the proximal end of the membrane than the respective distal tip of the respective substrate
   an adhesive disposed between the inner surface of each of the ten substrates and the membrane;
   and
   a reinforcement disposed atop each respective distal tip and an adjacent portion of the membrane that is disposed distal of the respective distal tip, the reinforcement not being disposed atop any portion of the ten contact electrodes, such that a thickness of the catheter balloon as measured from an inner surface of the membrane, through a respective distal tip, and to an outer surface of the reinforcement is about 0.0075 inches.

8. The catheter of claim 7, in which a maximum force required to withdraw the catheter balloon into the lumen is less than about 6 lbf.

9. The catheter of claim 8, in which the ten substrates each include side edges and an adhesive margin is disposed atop the side edges and the membrane.

10. The catheter of claim 9, in which the reinforcement comprises a portion of an unassembled membrane.

11. The catheter of claim 9, in which the reinforcement comprises an adhesive-margin tip.

\* \* \* \* \*